United States Patent [19]
Koeneman et al.

[11] Patent Number: 5,792,040
[45] Date of Patent: Aug. 11, 1998

[54] PATIENT INTERFACE DEVICE FOR GENERATING THERAPEUTIC MAGNETIC FIELDS

[75] Inventors: James B. Koeneman, Mesa; Michael R. Sheller, Tempe, both of Ariz.

[73] Assignee: OrthoLogic Corporation, Tempe, Ariz.

[21] Appl. No.: 717,648

[22] Filed: Sep. 23, 1996

[51] Int. Cl.⁶ .................................................. A61N 1/00
[52] U.S. Cl. ........................................ 600/13; 600/15
[58] Field of Search ................................ 600/9–15

[56] References Cited

U.S. PATENT DOCUMENTS

| | | | |
|---|---|---|---|
| 2,404,283 | 7/1946 | Gieringer | 128/413 |
| 4,456,001 | 6/1984 | Pescatore | 128/1.5 |
| 4,550,714 | 11/1985 | Talish et al. | 128/1.5 |
| 4,616,629 | 10/1986 | Moore | 128/1.5 |
| 4,635,643 | 1/1987 | Brown | 128/653 |
| 4,932,951 | 6/1990 | Liboff et al. | 606/13 |
| 5,139,474 | 8/1992 | Lamond et al. | 600/15 |
| 5,211,160 | 5/1993 | Talish et al. | 128/24 AA |
| 5,314,401 | 5/1994 | Tepper | 600/15 |

FOREIGN PATENT DOCUMENTS

| | | |
|---|---|---|
| 1314941 | 2/1987 | Canada . |
| 0 104 793 | 8/1983 | European Pat. Off. . |
| 2242362 | 10/1991 | United Kingdom ............. 600/15 |

*Primary Examiner*—John P. Lacyk
*Attorney, Agent, or Firm*—Dykema Gossett PLLC

[57] ABSTRACT

A patient interface device provides a single coil having two generally opposed flange regions which generate a large area, uniform magnetic field. The coil includes a magnetic field sensor for determining the magnetic field intensity between the flanges. The wire windings in the flanges may be distributed in various cross-sectional profiles.

24 Claims, 3 Drawing Sheets

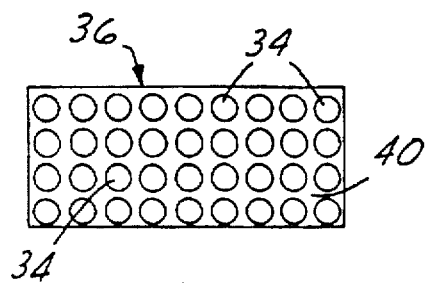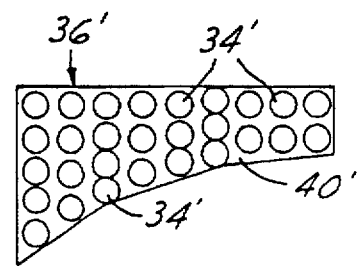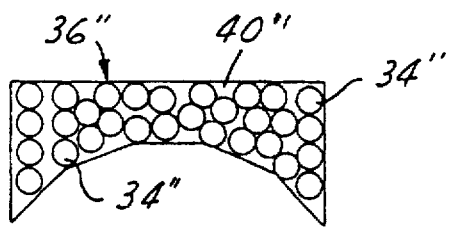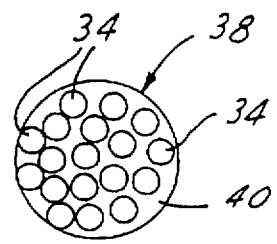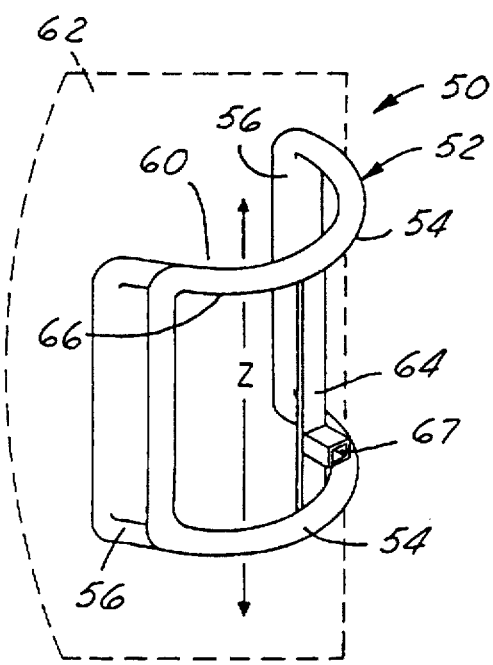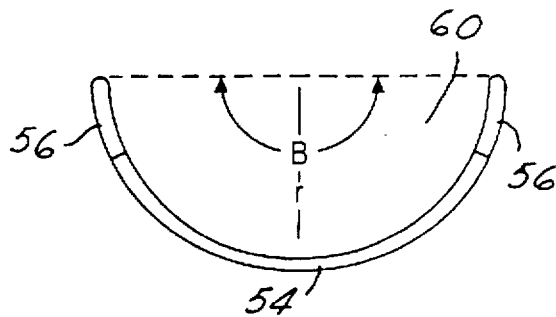

PATIENT INTERFACE DEVICE FOR GENERATING THERAPEUTIC MAGNETIC FIELDS

TECHNICAL FIELD

The present invention relates generally to apparatus for applying therapeutic magnetic fields and, more specifically, to single-coil patient interface devices for applying therapeutic magnetic fields.

BACKGROUND OF THE INVENTION

The scientific community has now widely accepted the benefits of magnetic field therapy for the treatment of certain medical conditions. In order for these therapeutic fields to be properly applied, patient interface devices have been designed which place one or more magnetic field generating coils adjacent a body region which is to be treated. An example of one type of patient interface device used in applying a therapeutic magnetic field is shown in U.S. Pat. No. 5,139,474 entitled, "Medical Treatment Device With Self-Centering Securing Members," which has been assigned to the assignee of the present invention. Therein, an apparatus is described which engages a region of a patient's body, such as a limb, in a manner which places a pair of coils in opposed relation relative to the region targeted for treatment. This prior art apparatus has a relatively rigid shell comprising two rigid shell halves which are hinged together at a single hinge axis. The two shell halves pivot away from each other to a non-treating position and pivot towards each other in a treatment position. Means are provided for securing the shell halves together in the treatment position. One coil is disposed in each shell half and the pair of coils are used to generate the therapeutic magnetic field. That is, a voltage of a given amplitude and frequency is applied to the coils to induce a current and produce a magnetic field. Resilient securing members extend inward from the shell halves and have a flexible backing that applies a force radially from the shell halves. The resilient securing members deform outward to conform to the anatomy of the region to which it is applied.

In published European patent application No. 104 793 an apparatus for equine limb treatment is described in which two electrical coil units are applied in opposed relation on a bandage wrapped around a limb which is to receive treatment. Each unit has a lining of a soft cushioning material such as a urethane foam and is held in place by a circumferential elastic strap.

In addition to opposed dual coil devices, single coil application of magnetic fields is also known. For example, in U.S. Pat. No. 4,616,629, entitled, "Coil Construction for Electromagnetic Treatment of an Afflicted Body Region," a coil is described which defines two U-shaped cavities. The two cavities are of unequal size which permits the device to be used interchangeable, i.e. one device can fit two different sizes of anatomical structures. And, Canadian Patent No. 1,314,941 discloses a treatment coil which is generally circular having outwardly spiraling multiple strands of conductors.

In order to provide the most effective treatment of an anatomical region, large area magnetic field coverage is desirable. From a review of the prior art it can be seen that the current single coil patient interface devices are limited in their ability to produce uniform magnetic fields over large areas. For example, as shown in FIGS. 1 and 1A of the drawings, in the case of a rectangular coil 20 the magnetic field decays very rapidly with distance from the coil.

Therefore, it would be desirable to provide a patient interface device which permits uniform therapeutic fields to be generated over large regions of space. The present invention provides a unique solution to the limitations inherent in prior art single coil devices.

SUMMARY OF THE INVENTION

The present invention provides an improved coil design for applying therapeutic magnetic fields to an anatomical region such as an arm or leg of a patient. The coil design of this invention is particularly well adapted for magnetic field treatment of bone. The present invention provides a large, uniform magnetic field in a precise location.

In one aspect, the present invention provides a single coil having multiple windings, wherein the coil includes two enlarged or flanged regions. In the flanged regions of the coil, the windings are spread or flattened to form a wider surface area which allows a wider area magnetic field to be produced at the flanges. The overall geometry of the coil is such that it is curved or otherwise configured to create a space or opening that receives the body region to be treated along an orientation axis. The curvature and orientation of the coil is such that the coil flanges are placed generally on opposite sides of the treatment region such that the field developed by the flanges occupies the space between the flanges and thus permeates the target tissue in a uniform manner. By having the windings distributed in a wider area in the flanges relative to the rest of the coil, a large uniform magnetic field can be developed precisely in the treatment region.

In still another aspect, the present invention provides a flanged coil which allows the profile of the applied field to be determined by the arrangement of the windings in the flanges. The wire distribution on the flanges may be rectangular in cross-section or in other conformations such as exponential or parabolic to control the profile of the applied field with greater accuracy.

Thus, in the broadest sense, the present invention provides a single-coil, magnetic-field patient interface device having a single coil of multiple windings. The windings are distributed in a small or narrow cross-sectional profile along the coil except for two generally opposed regions in which the windings are spread to provide a wide field-generating area. The coil is shaped to provide a space for receiving a region of the patient's body such as an arm or leg. The flanges are positioned generally on opposite sides of the treatment area. A number of coil shapes are provided.

In another aspect, the present invention provides a flanged single-coil patient interface device which has a magnetic field sensor for determining the field strength of the magnetic field in the target tissue between the flanges.

These and other objects and advantages of the present invention will be more fully appreciated in connection with the detailed description of the preferred embodiments of the invention with reference to the drawings.

BRIEF DESCRIPTION OF THE DRAWINGS

FIG. 3 of the drawings is a fragmentary view of FIG. 2, illustrating a cross-section through lines 3—3.

FIG. 4 of the drawings is a cross-sectional view of a flange of a coil in the present invention in an alternative arrangement.

FIG. 5 of the drawings is a cross-sectional view of a flange of a coil in the present invention in an alternative arrangement.

FIG. 6 is of the drawings is a fragmentary view of FIG. 2 along lines 6—6.

FIG. 7 of the drawings is a perspective view of a coil made in accordance with a preferred embodiment of the present invention.

FIG. 8 of the drawings is a diagrammatic top view of the coil depicted in FIG. 7.

DETAILED DESCRIPTION OF THE PREFERRED EMBODIMENTS OF THE INVENTION

The present invention is directed to a single coil patient interface device for use in applying a therapeutic magnetic field to a patient. While applications will typically be in the treatment of bone disorders, such as non-unions in man, other therapeutic applications as well as application in animals for veterinary science are also contemplated. The precise nature of the magnetic field so applied does not form a part of the present invention, but such fields are described in the prior art such as in U.S. Pat. Nos. 4,932,951, 5,067,940 and 5,160,591. The drawings referred to herein are not necessarily to scale and like numbers refer to like parts. The following is a description of preferred embodiments; other applications and coil geometries, including possible multiple coil adaptions of the present invention, may be deduced based on the teachings set forth by this disclosure.

Figure 1:
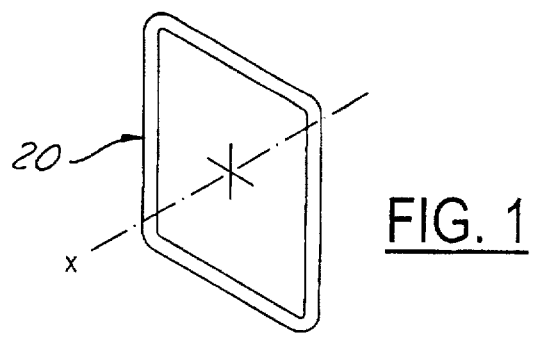
FIG. 1 of the drawings is a diagrammatic perspective view of a non-flanged coil.
Figure 1A:
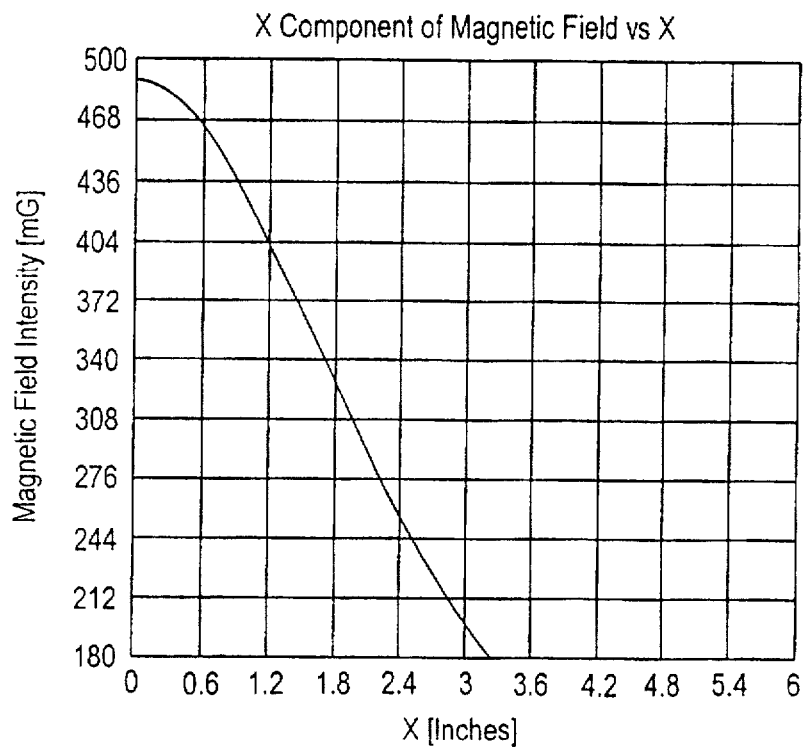
FIG. 1A is a graph which illustrates the decay of magnetic field intensity with distance along axis X of FIG. 1.

As stated above, FIGS. 1 and 1A illustrates the problem inherent with traditional single coil devices. A magnetic field is produced along the X axis on both sides of the coil. A region of tissue is placed on either side of the coil in the path of the axis. With this coil geometry, and as best shown in Figure 1A, the magnetic field which is developed by the coil decays very rapidly as the distance from the coil increases. Therefore, with a single coil, the field, and its therapeutic benefits, decays through the target tissue. The resultant field may be less effective in the regions distal of the coil. This decay phenomenon generally requires that two separate opposed coils be placed on opposite sides of the target region to create a field of more uniform strength.

Figure 2:
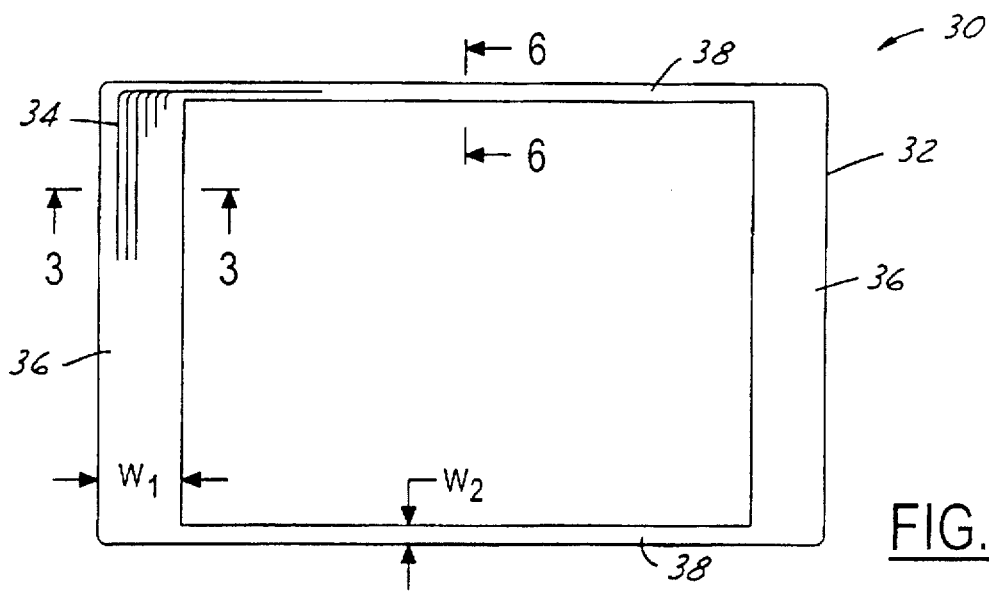
FIG. 2 of the drawings is a front elevational view of a coil made in accordance with the present invention having flanged treatment regions.

Referring now to FIG. 2 of the drawings, in the present invention, patient interface device 30 is shown comprising coil 32 having multiple windings of wire 34. FIG. 2 is a front projection of coil 32. That is, in order to describe the nature and structure of the windings FIG. 2 illustrates coil 32 with the coil in a single plane. In reality, and as shown in the remainder of the drawings, coil 32 is shaped such that a target tissue receiving space with an orientation axis is defined and such that the flanges are generally opposed to each other. Moreover, for ease of illustration, only a portion of wire 34 is shown in FIG. 2. It is to be understood that wire 34 is preferably a single piece or continuous strand of wire which has a beginning and an end which serve as terminals across which a voltage is applied. The number of turns of wire 34 in coil 32 may vary depending on a number of parameters such as the desired field intensity and the size of the coil. For most applications, however, the number of turns of wire 34 will be between about 200 and about 800. The wire may generally be any electrically conductive metal or metal alloy, but most preferred is single build copper magnet wire and may have a bondable insulation. Wire 34 is most typically referred to in gauges and for the present invention the wire gauges will between about 25 and about 31 U.S. Gauge (in diameter, about 0.454 to about 0.226 mm). As will be described more fully hereinafter, wire 34 is preferably insulated in the customary manner with polymeric wire insulation. One particularly preferred wire 34 for use in the present invention is single build copper magnet wire which may be obtained from MWS Industries of Westlake Village, Calif. Other wires may be suitable or desirable in a given application.

Coil 32 in FIG. 2 has two end regions or portions in which wire 34 is distributed to form flanges 36. In other words, in one embodiment the sides 38 of coil 32 have wire 34 distributed in a manner which has a surface area that is smaller than that of flanges 36, for example, as shown in FIG. 6 of the drawings. In FIG. 6 wire 34 is shown in a bundle that is generally circular in cross-section.

Since wire 34 is continuous, sides 38 serve to "connect" flanges 36. As best seen in FIGS. 2 and 3 of the drawings, wire 34 is redistributed as it enters flange regions 36 to have a greater field-generating surface area. Although the following ratios are not deemed critical it is preferred that width "$W_1$" of each flange 36 be from 2 to 5 times larger than the width "$W_2$" of each side region 38. For example if the width (or diameter) of each side 36 is 6 mm, the width of each flange 36 would be about 30 mm. In general, then, each flange 36 will have a length, a width and a depth. The width is preferably greater than the depth but less than the length.

As will be appreciated by those skilled in the art, the distribution profile of wire 34 in flanges 36 will affect the profile of the resultant magnetic field. The three preferred profiles (cross-sectional) for use in the presently invention are shown in FIGS. 3, 4 and 5 of the drawings. In FIG. 3 wire 34 is arranged in a generally rectangular cross-sectional distribution, with wire insulation 40 being shown separating electrically conductive wire 34. In FIG. 4 (corresponding parts shown as primes), an exponential cross-sectional distribution (generally triangular) is shown with one edge having a greater depth of windings than the other edge of flange 36. In still another arrangement of Flanges 36, FIG. 5 (corresponding parts shown as double primes) illustrates a parabolic distribution (u-shaped side) of wire 34", that is, flange 36" is thicker at its edges than in the middle.

With respect to the length of side portions 38 relative to the length of flanges 36, side portion 38 will generally be about 50% longer than flanges 36 to provide a proper anatomical fit, but the lengths may be the same or flanges 36 may actually be longer than sides 38 in some applications.

As stated, patient interface device 30 in the present invention is shaped to conform to an anatomical region and to place flanges 36 in generally opposed relation. Accordingly, several preferred shapes are disclosed herein. Although the illustrated shapes are preferred they are in no manner intended to be limiting.

Referring now to FIG. 7 of the drawings, a configuration of patient interface device 50 referred to herein as a half cylindrical coil with curved side flanges is shown having coil 52 with sides 54 and flanges 56. Wire 58 is again a single length of wire in multiple turns. As shown in FIG. 8, coil 52 is a half cylinder having a radius "r" which will typically be between about 50 mm and about 150 mm. Coil 52 defines a single tissue receiving space 60 in which a portion of the patient's body, for example the upper arm 62 (shown in phantom), is placed along the length of the orientation axis Z. Generally, coil 52 will be in direct contact with the patient. In some applications, coil 52 will be flexible such that it can be deformed to more precisely match the patient's anatomy. Sides 54 are linked with cross-bar 64 which houses the terminals or ends of wire 66 which comprises the windings of coil 52. Cross-bar has a plug in terminal 66 into which a magnetic field sensor 67 (shown only in FIG. 7) and a power supply may be attached. In addition, cross-bar 64 may support various displays and the like for patient monitoring and compliance information. Cross-bar 64 is generally formed of any non-magnetic material such as aluminum and may be attached to coil 52 through the use of an adhesive or non-magnetic screws or the like. The preferred sensor 67 is a magnetoresistive type sensor which may be obtained under the trade name $KMZ_1 0A_1$ from the Phillips Company of Sunnyvale, Calif. It will be appreciated that magnetic field components may be sensed by sensor 67 which can be used to calculate the magnetic field that permeates the subject in receiving space 60 between flanges 56.

Figure 9:
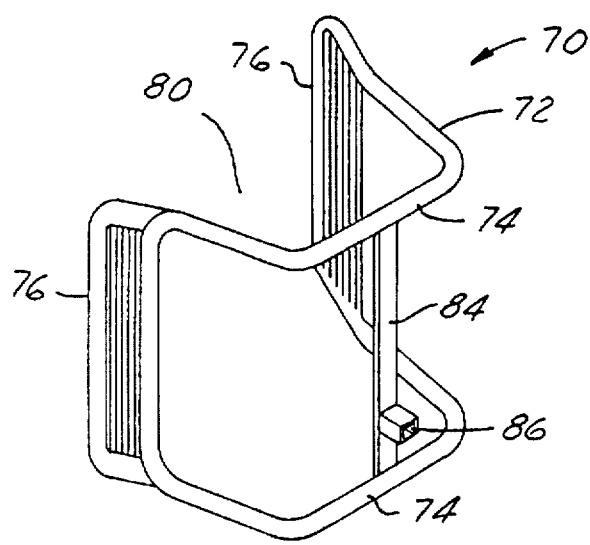
FIG. 9 of the drawings is a perspective view of a coil made in accordance with another preferred embodiment of the present invention.
Figure 10:
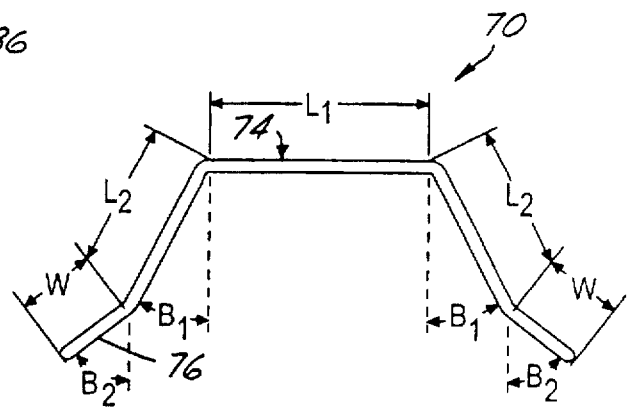
FIG. 10 of the drawings is a diagrammatic top view of the coil depicted in FIG. 9.

Referring now to FIG. 9 of the drawings, patient interface device 70 is a box coil with parallel side flanges and has coil 72 with sides 74 and flanges 76. Limb receiving space 80 is defined as in the previous embodiment. Cross-bar 84 again has plug-in receptacle 86 for insertion of a sensor and attachment of a power supply. Referring to FIG. 10 of the drawings, each side 74 has a length "L1"0 and a length "L2." The junction of these two segments defines an angle B1 which is preferably from about 0 to about 90 degrees and more preferably from about 0 to 45 degrees. Flanges 76 have a width "W" and are connected to the L2 segment of sides 74 by an angle B2 of from about 0 to about 90 degrees and more preferably from about 0 to 45 degrees.

Figure 11:
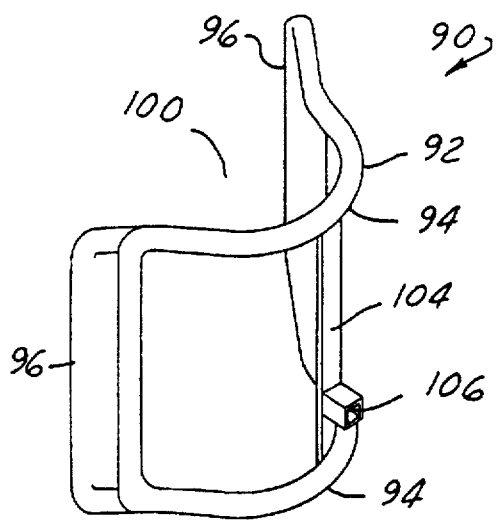
FIG. 11 of the drawings is a perspective view of a coil made in accordance with a another preferred embodiment of the present invention.
Figure 12:
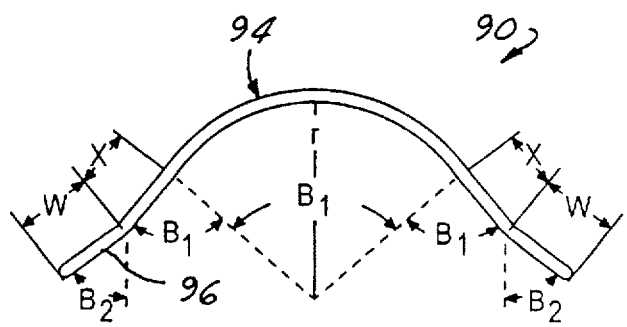
FIG. 12 of the drawings is a diagrammatic top view of the coil depicted in FIG. 11.

Referring now to FIG. 11 of the drawings, patient interface device 90 is a half cylindrical coil with parallel side flanges and has coil 92 with sides 94 and flanges 96. Limb receiving space 100 is defined as in the previous embodiment. Cross-bar 104 again has plug-in receptacle 106 for insertion of a magnetic field sensor and connection to a power supply. Referring to FIG. 12 of the drawings, each side 94 has a curved portion having a radius "r" which will generally be from about 50 to about 150 mm and a straight section having length "X." The intersection of the curved portion of end 94 with the straight section having length "X" will define an angle B1 of from about 0 to about 90 degrees and more preferably from about 0 to about 45 degrees. The junction of flange 96 with the straight section of length "X" will define an angle B2 of from about 0 to about 90 degrees.

It will appreciated that the coil designs of the present invention provide a number of features which can be adjusted in order to define a specific magnetic field distribution. These include the dimensions of the flanges, the radius of curved segments, the relative lengths of the various segments and the angles at segment junctions. It has been found that as the width of the flange increases, the magnetic field intensity becomes increasingly more uniform.

In one preferred embodiment, and referring now to FIG. 7 of the drawings, coil 52 is formed by winding insulated wire 66 around a mandrel or other form to create the general shape shown in the Figure. Once completed, a light spray of isopropyl alcohol is applied. The coil is then allowed to air dry. The insulation of wire 66 softens in this solution and congeals to form an electrically insulating matrix 40 as best shown in FIG. 3 of the drawings. A house or wrap (not shown) may be used to encase coil 52 if desired.

Thus, it is apparent that there has been provided in accordance with the invention a method and apparatus that fully satisfies the objects, aims and advantages set forth above. While the invention has been described inconnection with specific embodiments thereof, it is evident that may alternatives, modifications, and variations will be apparent to those skilled in the art in light of the foregoing description. Accordingly, it is intended to embrace all such alternative, modifications and variations that fall within the spirit and broad scope of the appended claims.

What is claimed is:

1. A patient interface device for generating a therapeutic magnetic field, comprising:
   a single coil of multiple turns of an electrically conductive wire, said coil having two flange regions interconnected by two sides, each of said sides having a first width, said flange regions each having a second width greater than the first width, each flange defining a wide area treatment surface for generating a therapeutic magnetic field.

2. The patient interface device recited in claim 1, wherein said flange has a profile with a half cylinder shape.

3. The patient interface device recited in claim 1, wherein said flange has a profile with a box shape.

4. The patient interface device recited in claim 1, wherein said flange has a profile with a half cylinder shape and said flanges are substantially parallel.

5. The patient interface device recited in claim 1, wherein said coil includes a housing formed of a non-magnetic material which encases said wire.

6. The patient interface device recited in claim 1, wherein said wire is copper.

7. The patient interface device recited in claim 1, wherein said device further includes a magnetic field sensor mounted on said coil.

8. The patient interface device recited in claim 7, wherein said flange regions are interconnected by a pair of parallel spaced patient-engaging portions and wherein said magnetic field sensor is disposed on a support member which is attached to said parallel spaced patient-engaging portions, said support member spanning a space between said parallel spaced patient-engaging portions.

9. A patient interface device which is adapted to engage an anatomical region of a patient, said patient interface device comprising:
   a coil having multiple turns of wire;
   said coil having a first flange portion which defines a first principal application surface and a second flange portion which defines a second principal application surface;
   said coil further having two extended portions which interconnect said first and second flange portions;
   said first and second flange portions each having a length, a width and a depth, said width being coextensive with said principal application surface and said width being larger than said depth and smaller than said length;
   said multiple turns of wire being arranged in said first and second flange portions such that said wire turns form a wide-area magnetic field generating surface in each of said flange portions; and terminals attached to each end of said wire for permitting said wire to be connected to an electrical power source.

10. The patient interface device recited in claim 9, further including a cross-bar spanning said two extended portions and a magnetic field sensor positioned on said cross-bar.

11. The patient interface device recited in claim 9, wherein said flange portions are curved.

12. The patient interface device recited in claim 9, wherein said flange portions are straight.

13. The patient interface device recited in claim 9, wherein each of said extended portions has at least two segments.

14. The patient interface device recited in claim 13, wherein at least one of said segments of each of said extended portions is curved.

15. The patient interface device recited in claim 13, wherein both of said segments of each of said extended portions are straight.

16. The patient interface device recited in claim 13, wherein one of said segments of each of said extended portions is curved and one of said segments is straight.

17. The patient interface device recited in claim 16, wherein said straight segments are connected to said flange portions.

18. The patient interface device recited in claim 10, wherein said magnetic field sensor is a magnetoresistive sensor.

19. A coil adapted to applying a therapeutic magnetic field to an appendage, said coil comprising:

a continuous wire wound as multiple windings in a ring configuration, said coil having an orientation axis along the appendage over which said coil is placed;

said ring configuration defining a pair of connecting portions at opposite ends of the coil with each of said connecting portions being sufficiently large to partially circumscribe the appendage, said connecting portions being spaced from each other along the orientation axis, said connecting portions being formed of a plurality of parallel windings; and said ring configuration further defining a pair of lateral flanges positioned along said orientation axis, said pair of flanges being formed of the multiple windings and being connected together by said connecting portions, said lateral flanges having a greater magnetic field generating surface area than said connecting portions.

20. The coil for applying a therapeutic magnetic field recited in claim 19, further including an associated magnetic field sensor for determining the strength of the magnetic field between said pair of lateral flanges.

21. The coil for applying a therapeutic magnetic field recited in claim 19, wherein the windings in said pair of flanges are parallel to each other and have a rectangular cross-section.

22. The coil for applying a therapeutic magnetic field recited in claim 19, wherein the windings in said pair of flanges are parallel to each other and define one U-shaped cross-sectional region.

23. The coil for applying a therapeutic magnetic field recited in claim 19, wherein the windings in said pair of flanges are parallel to each other and have a generally exponential cross-section.

24. A patient interface device for generating a therapeutic magnetic field, comprising:

a single coil of multiple turns of an electrically conductive wire, said coil having two interconnected flange regions, said flange regions each defining a wide area treatment surface for generating a therapeutic magnetic field, and a magnetic field sensor mounted on said coil, said flange regions are interconnected by a pair of parallel spaced patient-engaging portions and wherein said magnetic field sensor is disposed on a support member which is attached to said parallel spaced patient-engaging portions, said support member spanning said space between said parallel spaced patient-engaging portions.

* * * * *